(12) United States Patent
Kumada et al.

(10) Patent No.: US 8,846,148 B2
(45) Date of Patent: Sep. 30, 2014

(54) COMPOSITION FOR CHEMICAL VAPOR DEPOSITION FILM-FORMATION AND METHOD FOR PRODUCTION OF LOW DIELECTRIC CONSTANT FILM

(75) Inventors: Teruhiko Kumada, Chiyoda-ku (JP); Hideharu Nobutoki, Chiyoda-ku (JP); Naoki Yasuda, Chiyoda-ku (JP); Tetsuya Yamamoto, Nishinomiya (JP); Yasutaka Nakatani, Himeji (JP); Takuya Kamiyama, Takatsuki (JP)

(73) Assignee: Nippon Shokubai Co., Ltd., Osaka (JP)

( * ) Notice: Subject to any disclaimer, the term of this patent is extended or adjusted under 35 U.S.C. 154(b) by 616 days.

(21) Appl. No.: 12/084,568

(22) PCT Filed: Nov. 15, 2006

(86) PCT No.: PCT/JP2006/323251
§ 371 (c)(1),
(2), (4) Date: May 6, 2008

(87) PCT Pub. No.: WO2007/058365
PCT Pub. Date: May 24, 2007

(65) Prior Publication Data
US 2009/0232987 A1    Sep. 17, 2009

(30) Foreign Application Priority Data

Nov. 17, 2005  (JP) .................................. 2005-333077
Nov. 18, 2005  (JP) .................................. 2005-334494

(51) Int. Cl.
| | | |
|---|---|---|
| C23C 16/00 | (2006.01) |
| C07F 5/02 | (2006.01) |
| C23C 16/30 | (2006.01) |
| H01L 21/314 | (2006.01) |
| C23C 16/34 | (2006.01) |
| H01L 21/318 | (2006.01) |

(52) U.S. Cl.
CPC ............... C23C 16/342 (2013.01); C07F 5/02 (2013.01); C23C 16/30 (2013.01); H01L 21/314 (2013.01); H01L 21/318 (2013.01)
USPC .......... 427/255.394; 427/255.28; 427/255.38; 568/3; 564/10

(58) Field of Classification Search
USPC ............. 427/255.28, 255.38, 255.394; 568/3; 564/10; 106/287.27
See application file for complete search history.

(56) References Cited

U.S. PATENT DOCUMENTS

| | | | |
|---|---|---|---|
| 4,150,097 A * | 4/1979 | Hough et al. ................. 423/285 |
| 5,175,020 A * | 12/1992 | Doellein et al. .............. 427/569 |
| 7,671,473 B2 * | 3/2010 | Kumada et al. .............. 257/758 |
| 7,692,043 B2 * | 4/2010 | Yamamoto et al. ............... 568/3 |
| 7,863,749 B2 * | 1/2011 | Gates et al. .................... 257/759 |
| 2002/0053653 A1 | 5/2002 | Tsunoda et al. |
| 2002/0058142 A1 | 5/2002 | Tsunoda |
| 2002/0177002 A1 | 11/2002 | Fujino et al. |
| 2003/0100175 A1 * | 5/2003 | Nobutoki et al. ............. 438/623 |
| 2005/0177002 A1 | 8/2005 | Yamamoto et al. |
| 2005/0181628 A1 * | 8/2005 | Nobutoki et al. ............. 438/778 |
| 2006/0110610 A1 | 5/2006 | Matsutani et al. |

FOREIGN PATENT DOCUMENTS

| | | |
|---|---|---|
| EP | 0 510 567 A2 | 10/1992 |
| JP | 2000-340689 A | 12/2000 |
| JP | 2001-015496 A | 1/2001 |
| JP | 2003-119289 A | 4/2003 |
| JP | 2004-140341 A | 5/2004 |
| JP | 2004-186649 A | 7/2004 |
| JP | 2005-167044 A | 6/2005 |
| JP | 2005-179232 A | 7/2005 |
| WO | WO 2005/035824 A1 | 4/2005 |

OTHER PUBLICATIONS

Machine translation of JP 2004-186649 A, Advanced Industrial Property Network, Japan Patent Office, [online], [retrieved on Jun. 3, 2011]. Retrieved from the Internet: <URL: http://dossier1.ipdl.inpit.go.jp/AIPN/odse_top_dn.ipdl?N0000=7400 >.*
Machine translation of JP 2005-167044 A, Advanced Industrial Property Network, Japan Patent Office, [online], [retrieved on Jun. 3, 2011]. Retrieved from the Internet: <URL: http://dossier1.ipdl.inpit.go.jp/AIPN/odse_top_dn.ipdl?N0000=7400 >.*
Wideman et al, "Convenient Procedures for the Laboratory Preparation of Borazine" Inorg. Chem. 1995,34, pp. 1002-1003.*

(Continued)

*Primary Examiner* — Dennis Cordray
(74) *Attorney, Agent, or Firm* — Buchanan Ingersoll & Rooney PC

(57) ABSTRACT

A composition for chemical vapor deposition film-formation comprising a borazine compound represented by the Chemical Formula 1 satisfying at least one of a condition that content of each halogen atom in the composition is 100 ppb or less or a condition that content of each metal element in the composition is 100 ppb or less. In the Chemical Formula 1, $R^1$ may be the same or different, and is hydrogen atom, alkyl group, alkenyl group or alkynyl group, and at least one thereof is hydrogen atom; $R^2$ may be the same or different, and is hydrogen atom, alkyl group, alkenyl group or alkynyl group, and at least one thereof is alkyl group, alkenyl group or alkynyl group.

[Chemical Formula 1]

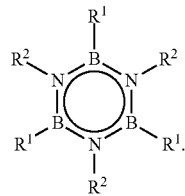

4 Claims, No Drawings

(56) References Cited

OTHER PUBLICATIONS

Office Action (Non-Final Rejection) dated Oct. 15, 2010, and issued by the Korean Intellectual Property Office in corresponding Korean Patent Application No. 10-2008-7011655, and English language translation thereof.
Office Action issued Dec. 4, 2009 in corresponding Chinese Patent Application No. 2006800426135, and English translation thereof.
Supplementary European Search Report issued Feb. 23, 2010 in corresponding European Patent Application No. 06823488.9.
International Search Report for PCT/JP2006/323251, Feb. 13, 2007.
Written Opinion for PCT/JP2006/323251, Feb. 13, 2007.
Office Action ("Notice of Examination Opinion") issued Jun. 21, 2012 in corresponding Taiwan Patent Application No. 95142339, together with an English translation thereof.

* cited by examiner

COMPOSITION FOR CHEMICAL VAPOR DEPOSITION FILM-FORMATION AND METHOD FOR PRODUCTION OF LOW DIELECTRIC CONSTANT FILM

This application is a 371 of PCT/JP2006/323251, filed Nov. 15, 2006 and claims priority to Japanese Application No. 2005-333077, filed Nov. 17, 2005, and Japanese Application No. 2005-334494, filed Nov. 18, 2005.

BACKGROUND OF THE INVENTION

1. Field of the Invention

The present invention relates to a low dielectric constant film to be used as an interlayer insulation film, a barrier metal layer, an etch stopper layer for LSI or the like. More specifically, the present invention relates to a composition for chemical vapor deposition film-formation and a method for production of a low dielectric constant film using the same.

2. Description of Related Art

Along with grading up in performance of information technology devices, the design rule of LSI has been becoming more and more finer every year. In the production of LSI having a fine design rule, a material as a component of the LSI must be one that has a high performance and fulfills a function even on a fine LSI.

For example, as for a material to be used as an interlayer insulation film in LSI, a high dielectric constant tends to cause signal delay. In a fine LSI, the signal delay influences particularly greatly. Consequently, development of a novel low dielectric constant material, which can be used as an interlayer insulation film, has been demanded. In addition, in order to be used as an interlayer insulation film, the material must be, not only low in dielectric constant, but also superior in properties such as moisture resistance, heat resistance and mechanical strength.

As a material to meet such demand, a borazine compound having a borazine ring skeleton in a molecule has been proposed (see, for example, JP-A-2000-340689). Since a compound having a borazine ring skeleton has a small molecular polalizability, a film to be formed has a low dielectric constant. Moreover, the film to be formed is superior in heat resistance. As the borazine compound, various compounds have been proposed up to now. For example, a borazine compound, which is substituted by an alkyl group at the site of boron, has very superior properties as a low dielectric constant material (see, for example, JP-A-2003-119289). Further, various production methods of thin film using the borazine compound have been proposed (see, for example, JP-A-2004-186649).

BRIEF SUMMARY OF THE INVENTION

In view of grading up in performance of information technology devices and the like, it is actual state that further improvement is demanded for performance, reliability and the like of a thin film formed using a borazine compound.

Consequently, an object of the present invention is to provide a means, which can improve properties such as low dielectric property and mechanical strength of a thin film produced from a borazine-ring-containing compound.

The present invention provides a composition for chemical vapor deposition film-formation satisfying at least one condition selected from the group consisting of a condition that the composition comprises a borazine compound represented by the Chemical Formula 1 and content of each halogen element in the composition is 100 ppb or less, a condition that the composition comprises a borazine compound represented by the Chemical Formula 2 and content of each halogen element in the composition is 10 ppm or less, and a condition that the composition comprises a borazine compound represented by the Chemical Formula 3 and content of each metal element in the composition is 100 ppb or less.

[Chemical Formula 1]

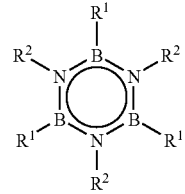

wherein $R^1$ independently represents hydrogen atom, alkyl group, alkenyl group or alkynyl group, and at least one thereof is hydrogen atom; $R^2$ independently represents hydrogen atom, alkyl group, alkenyl group or alkynyl group, and at least one thereof is alkyl group, alkenyl group or alkynyl group.

[Chemical Formula 2]

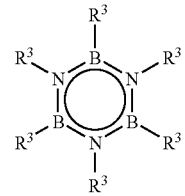

wherein $R^3$ independently represents alkyl group, alkenyl group or alkynyl group.

[Chemical Formula 3]

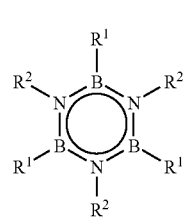

wherein $R^1$ independently represents hydrogen atom, alkyl group, alkenyl group or alkynyl group; $R^2$ independently represents hydrogen atom, alkyl group, alkenyl group or alkynyl group, and at least one thereof is alkyl group, alkenyl group or alkynyl group.

In addition, the present invention provides a method for producing a low dielectric constant film where the above-described composition is formed to a film using a chemical vapor deposition method under the prescribed conditions.

A thin film to be produced from the composition for chemical vapor deposition film-formation of the present invention is superior in properties such as low dielectric property and mechanical properties. Consequently, when the thin film is applied to an interlayer insulation layer of a semiconductor, signal transfer rate and reliability of the semiconductor device can be improved.

DETAILED DESCRIPTION OF THE INVENTION

First aspect of the present invention relates to a composition for chemical vapor deposition film-formation having lower content of each halogen atom to be used for producing a thin film, which is superior in properties such as low dielectric constant property and mechanical strength. More specifically, first aspect of the present invention is a composition for chemical vapor deposition film-formation comprising a borazine compound represented by the Chemical Formula 1 and content of each halogen element in the composition is 100 ppb or less.

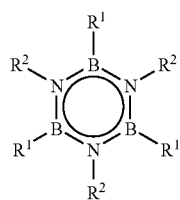

[Chemical Formula 1]

wherein $R^1$ independently represents hydrogen atom, alkyl group, alkenyl group or alkynyl group, and at least one thereof is hydrogen atom; $R^2$ independently represents hydrogen atom, alkyl group, alkenyl group or alkynyl group, and at least one thereof is alkyl group, alkenyl group or alkynyl group.

Further, first aspect of the present invention is also a composition for chemical vapor deposition film-formation comprising a borazine compound represented by the Chemical Formula 2 and content of each halogen element in the composition is 10 ppm or less.

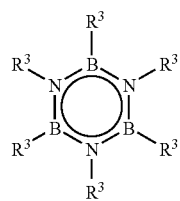

[Chemical Formula 2]

wherein $R^3$ independently represents alkyl group, alkenyl group or alkynyl group.

Content of each halogen element in the film-forming composition comprising a borazine compound represented by the Chemical Formula 1 is 100 ppb or less, preferably 50 ppb or less, and more preferably 10 ppb or less. Content of each halogen element in the film-forming composition comprising a borazine compound represented by the Chemical Formula 2 is 10 ppm or less, preferably 5 ppm or less, and more preferably 2 ppm or less. Use of a composition comprising a borazine compound with lower content of halogen element as a raw material reduces content of halogen element in a low dielectric constant film to be formed and water absorption coefficient of the film, resulting in a film having a low dielectric constant. Lower limit of the content of halogen element is not particularly limited. Generally, the lower limit is preferably as low as possible, because these elements are impurities. When plural halogen elements are contained, a content of each element may be within the above range.

Content of halogen element can be calculated by measuring the film-forming composition comprising a borazine compound. Halogen element is presumed to be actually present in a form of a halogen-containing compound or a halogen molecule, but in the present invention, halogen content is defined as an amount of the element converted from an amount of halogen compounds contained in the composition. More specifically, content of each halogen element mixed in a composition can be measured using an ion chromatography. Type and measuring conditions of the ion chromatography are not particularly limited. In this connection, when measured value varies depending on an equipment to be used or measuring conditions, a value measured by the method described in Examples is employed as a content of halogen element.

Second aspect of the present invention relates to a composition for chemical vapor deposition film-formation having lower content of each metal element to be used for producing a thin film, which is superior in properties such as low dielectric constant property and mechanical strength. More specifically, second aspect of the present invention is a composition for chemical vapor deposition film-formation comprising a borazine compound represented by the Chemical Formula 3 and content of each metal element in the composition is 100 ppb or less.

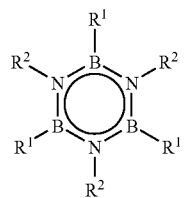

[Chemical Formula 3]

wherein $R^1$ independently represents hydrogen atom, alkyl group, alkenyl group or alkynyl group; $R^2$ independently represents hydrogen atom, alkyl group, alkenyl group or alkynyl group, and at least one thereof is alkyl group, alkenyl group or alkynyl group.

Preferably, second aspect of the present invention is a composition for chemical vapor deposition film-formation comprising a borazine compound of the Chemical Formula 3, wherein at least one of $R^1$ is a hydrogen atom, and content of each metal element in the composition is 100 ppb or less. In this connection, the borazine compound of the Chemical Formula 3, wherein at least one of $R^1$ is a hydrogen atom, corresponds to a borazine compound represented by the Chemical Formula 1.

Preferably, second aspect of the present invention is a composition for chemical vapor deposition film-formation comprising a borazine compound of the Chemical Formula 3, wherein $R^1$ and $R^2$ are each independently alkyl group, alkenyl group or alkynyl group, and content of each metal element is 100 ppb or less. In this connection, the borazine compound of the Chemical Formula 3, wherein $R^1$ and $R^2$ are each independently alkyl group, alkenyl group or alkynyl group, corresponds to a borazine compound represented by the Chemical Formula 2.

Content of each metal element in the film-forming composition is 100 ppb or less, preferably 50 ppb or less, and more preferably 10 ppb or less. Use of a composition comprising a borazine compound containing lower content of metal element as a raw material reduces content of metal element in the low dielectric constant film to be formed therewith, and leak current of the film, resulting in a film having a low dielectric constant. Lower limit of the content of metal element is not particularly limited. Generally, lower limit is preferably as low as possible, because these elements are impurities. When plural metal elements are contained, a content of each element may be within the above range.

Content of metal element can be calculated by measuring the film-forming composition comprising a borazine compound. Metal element is presumed to be actually present in various forms such as an elementary substance and metal compounds, but in the present invention, metal content is defined as an amount of metal atom contained in the composition. More specifically, content of metal element contained in a composition can be measured using a high-frequency plasma emission spectrometer (ICP), an ICP-MS, or an atomic absorption spectrometry. Type and measuring conditions of each measuring equipment are not particularly limited. In this connection, when measured value varies depending on an equipment to be used or measuring conditions, a value measured by the method described in Examples is employed as a content of metal element.

A thin film to be formed using a borazine compound represented by any one of the Chemical Formulas 1 to 3 has a low dielectric constant and high heat resistance. Moreover, when content of halogen element contained in a film-forming composition to be used as a raw material is low, a film having a low dielectric constant is obtained due to a low water absorption coefficient of the film. In addition, when content of each metal element contained in a film-forming composition to be used as a raw material is low, a film having a low dielectric constant is obtained due to a low leak current of the film.

Since the first and the second aspects of the present invention are similar to each other except that content of halogen element or metal element contained in the composition is defined, both will be explained together in the following description. In this connection, both of the prescription for halogen element and the prescription for metal element may be satisfied at the same time, as a matter of course.

In the Chemical Formula 1, $R^1$ and $R^2$ are each hydrogen atom, alkyl group, alkenyl group or alkynyl group, and at least one of $R^1$ is hydrogen atom and also at least one of $R^2$ is alkyl group, alkenyl group or alkynyl group.

Alkyl group may be linear, branched or cyclic. Number of carbon atom possessed by alkyl group is not particularly limited, but preferably 1 to 8, more preferably 1 to 4, and further more preferably 1 to 2, in view of sublimation purification or distillation purification. Specific examples of alkyl group include, for example, methyl, ethyl, propyl, isopropyl, butyl, isobutyl, sec-butyl, tert-butyl, pentyl, isopentyl, neopentyl, hexyl, heptyl, octyl, nonyl, decyl, cyclopropyl, cyclopentyl and cyclohexyl. An alkyl group other than these groups may be used.

Alkenyl group may be linear, branched or cyclic. Number of carbon atom possessed by alkenyl group is not particularly limited, but preferably 2 to 5, and more preferably 2 to 3, in view of purification by sublimation or distillation. Specific examples of alkenyl group include, for example, vinyl, allyl, propenyl, isopropenyl, 1-butenyl, 2-butenyl, 3-butenyl, 1-hexenyl, 2-hexenyl, 3-hexenyl, 4-hexenyl, 5-hexenyl, cyclopentenyl, cyclohexenyl and cyclooctenyl. An alkenyl group other than these groups may be used.

Alkynyl group may be linear, branched or cyclic. Number of carbon atom possessed by alkynyl group is not particularly limited, but preferably 2 to 5, and more preferably 2 to 3, in view of purification by sublimation or distillation. Specific examples of alkynyl group include, for example, ethynyl, 2-propynyl and 2-butynyl. An alkynyl group other than these groups may be used.

$R^1$ and $R^2$ may be each the same or different, but every $R^1$ is preferably hydrogen atom, in view of yield in the synthesis reaction, easiness in handling, physical properties when used for a semiconductor material and the like. Similarly, every $R^2$ is preferably an alkyl group. More preferably, the borazine compound is N,N',N"-trialkylborazine.

Specific examples of such a borazine compound include, for example, N,N',N"-trimethylborazine and N,N',N"-triethylborazine.

In the Chemical Formula 2, $R^3$ is alkyl group, alkenyl group or alkynyl group. Specific form of $R^3$ is the same to that of alkyl group, alkenyl group or alkynyl group in $R^1$ and $R^2$ of the Chemical Formula 1.

In the Chemical Formula 2, $R^3$ may be the same or different, but every $R^3$ is preferably an alkyl group, in view of yield in the synthesis reaction, easiness in handling, physical properties when used for a semiconductor material and the like. More preferably, the borazine compound is hexaalkylborazine or B,B',B"-triethyl-N,N',N"-trimethylborazine.

Specific examples of the borazine compound of the Chemical Formula 2 include, for example, hexamethylborazine, hexaethylborazine, hexa(n-propyl)borazine, hexa(iso-propyl)borazine, hexa(n-butyl)borazine, hexa(sec-butyl)borazine, hexa(iso-butyl)borazine, hexa(tert-butyl)borazine, hexa(1-methylbutyl)borazine, hexa(2-methylbutyl)borazine, hexa(neo-pentyl)borazine, hexa(1,2-dimethylpropyl)borazine, hexa(1-ethylpropyl)borazine, hexa(n-hexyl)borazine, hexacyclohexylborazine, B,B',B"-trimethyl-N,N',N"-triethylborazine, B,B',B"-trimethyl-N,N',N"-tri(n-propyl)borazine, B,B',B"-trimethyl-N,N',N"-tri(iso-propyl)borazine, B,B',B"-triethyl-N,N',N"-trimethylborazine, B,B',B"-triethyl-N,N',N"-tri(n-propyl)borazine, B,B',B"-triethyl-N,N',N"-tri(iso-propyl)borazine, B,B',B"-tri(iso-propyl)-N,N',N"-trimethylborazine, B,B',B"-tri(iso-propyl)-N,N',N"-triethylborazine, hexavinylborazine, hexaallylborazine, hexapropenylborazine, hexaisopropenylborazine, hexa(1-butenyl)borazine, hexa(2-butenyl)borazine, hexa(3-butenyl)borazine, hexa(1-hexenyl)borazine, B,B',B"-trimethyl-N,N',N"-trivinylborazine, B,B',B"-trimethyl-N,N',N"-triallylborazine, B,B',B"-trimethyl-N,N',N"-tripropenylborazine, B,B',B"-trivinyl-N,N',N"-trimethylborazine, B,B',B"-triallyl-N,N',N"-trimethylborazine, B,B',B"-tripropenyl-N,N',N"-trimethylborazine, hexaethynylborazine, hexa(2-propynyl)borazine, hexa(2-butynyl)borazine, B,B',B"-trimethyl-N,N',N"-triethynylborazine, B,B',B"-trimethyl-N,N',N"-tri(2-propynyl)borazine, B,B',B"-trimethyl-N,N',N"-tri(2-butynyl)borazine, B,B',B"-triethynyl-N,N',N"-trimethylborazine, B,B',B"-tri(2-propynyl)-N,N',N"-trimethylborazine and B,B',B"-tri(2-butynyl)-N,N',N"-trimethylborazine.

In the Chemical Formula 3, $R^1$ and $R^2$ are each hydrogen atom, alkyl group, alkenyl group or alkynyl group, and at least one of $R^2$ is alkyl group, alkenyl group or alkynyl group. Specific form of alkyl group, alkenyl group or alkynyl group is the same to that of borazine compound represented by the Chemical Formula 1.

The film-forming composition may contain other component to improve film properties if necessary, or may be substantially a composition comprising the borazine compound.

Third aspect of the present invention is a method for producing a low dielectric constant film wherein the compositions of the first aspect or the second aspect of the present invention is formed to a film using a chemical vapor deposition (CVD) method. By using the composition of the present invention, a thin film superior in low dielectric constant property can be obtained. In addition, when a CVD method is used as a film-forming method, mechanical strength of the film is improved due to increased cross-linking density by the borazine compound in the film. This results in improved signal transfer speed and reliability of a semiconductor device.

Hereinafter, production steps of the present invention will be described in the order of the steps.

Firstly, a composition for chemical vapor deposition film-formation comprising a borazine compound represented by the Chemical Formula 1 to be used as a raw material is prepared.

[Chemical Formula 1]

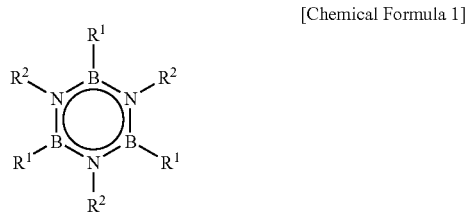

Explanation of the Chemical Formula 1, prescriptions and measuring methods for content of halogen element and content of metal element are as previously described, and will be omitted here.

The borazine compound of the Chemical Formula 1 can be synthesized, for example, by a reaction of an alkylamine hydrochloride and an alkali boron hydride in a solvent as shown in the following Reaction Scheme 1 (see, for example, Howard Steinberg, ORGANOBORON CHEMISTRY, Volume 2, Interscience Publishers, p. 221-222).

[Reaction Scheme 1]

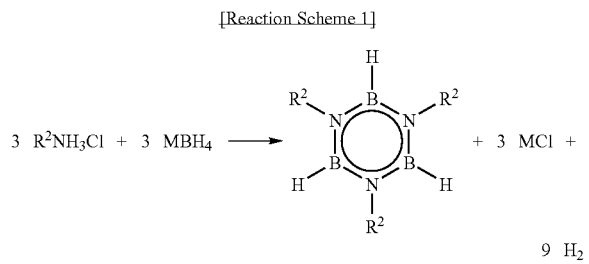

wherein $R^2$ is defined in the same way as the above and M means an alkali metal selected from the group consisting of potassium, sodium and lithium.

In the Reaction Scheme 1, the alkylamine salt is in a form of hydrochloride, but not limited only to such a form. For example, thealkylamine salt may beprovidedin a form of sulfate or the like.

The alkylamine salt and the alkali boron hydride to be used may be selected corresponding to a structure of the borazine compound to be synthesized. For example, when a borazine compound where alkyl group, alkenyl group or alkynyl group is contained as a part of the substituents $R^1$, which are each hydrogen atom in the Reaction Scheme 1, is intended to be synthesized, for example, the compound obtained from the above Reaction Scheme 1 may be reacted with a Grignard reagent.

Mixing ratio of an alkali boron hydride and an alkylamine salt is not particularly limited. To cite one example, when 1 mole of an alkylamine salt is used, an amount of an alkali boron hydride to be used is preferably 1 to 1.5 moles.

Also, solvent for the synthesis is not particularly limited, and a known solvent, which is conventionally used in the synthesis of a borazine compound, can be similarly used, as appropriate. Solvents to be used in the synthesis of a borazine compound include, for example, ethers such as monoglyme, diglyme, triglyme and tetraglyme; aromatic hydrocarbons such as benzene, toluene and xylene; alicyclic hydrocarbons such as cyclohexane, tetralin and decalin.

Reaction conditions of an alkylamine salt and an alkali boron hydride are not particularly limited. Reaction temperature is preferably 20 to 250° C., more preferably 50 to 240° C., and further more preferably 100 to 220° C. When reaction is carried out in the above range, amount of hydrogen gas to be generated can be easily controlled. Reaction temperature can be measured using a temperature sensor such as K type thermo couple.

After obtaining a borazine compound of the Chemical Formula 1 by the synthesis, the borazine compound is purified. Purification can be performed by both of sublimation purification and distillation purification. Purification may be carried out only by one means of either sublimation purification or distillation purification. Sublimation purification is a purifying method where impurities and a desired substance are separated using a difference in sublimation temperature of each compound. Embodiment of sublimation purification is not particularly limited. Mode of sublimation purification equipment may be selected, as appropriate, depending on production scale and production atmosphere of a borazine compound. For example, strict execution of temperature control by flowing a gas can lead to improvement in purity of the desired substance to be obtained. Distillation purification is a purifying method where impurities and a desired substance are separated by distillation. Impurities and a desired substance are separated using a difference in volatility of each component. Embodiment of distillation is also not particularly limited, and size and type of a distillation purification apparatus may be decided depending on atmosphere and scale. Preferable distillation purification is that by repeating simple distillation twice or more or use of a multistage distillation column.

Alternatively, a composition for chemical vapor deposition film-formation comprising a borazine compound represented by the Chemical Formula 2 is prepared.

[Chemical Formula 2]

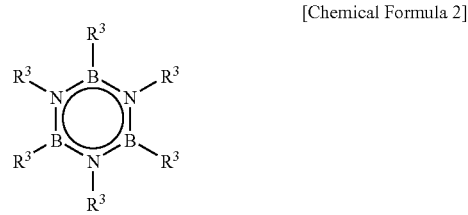

Explanation of the Chemical Formula 2, prescriptions and measuring methods of content of halogen element and content of metal element are as previously described, and will be omitted here.

The borazine compound represented by the Chemical Formula 2 can be synthesized by subjecting a halogenated borazine compound represented by the Chemical Formula 4 to a reaction with a Grignard reagent.

[Chemical Formula 4]

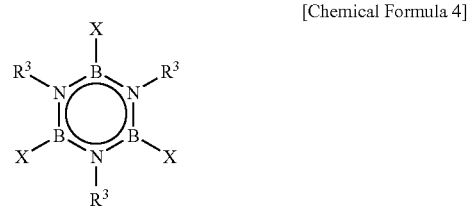

wherein $R^3$ is as defined previously, and X is halogen atom; Procurement route of the halogenated borazine compound is not particularly limited. When the halogenated borazine compound is synthesized, known knowledge can be referred to, as appropriate. For example, the synthesis process described in D. T. HAWORTH, Inorganic Synthesis, 10, 43 (1971) can be employed. When the compound is synthesized for oneself, for example, boron trichloride ($BCl_3$) and an amine compound represented by $R^3NH_3X$ are reacted. In the reaction of boron trichloride and an amine compound, an embodiment where boron trichloride is added into a solvent suspended with an amine compound is preferable. Solvents that can be used include, for example, o-xylene, m-xylene, p-xylene, monochlorobenzene, o-dichlorobenzene and m-dichlorobenzene. Atmosphere around the reaction solution is not particularly limited, but preferably atmosphere around the reaction solution is replaced with an inert gas such as nitrogen and argon.

As a Grignard reagent, various Grignard reagents such as $CH_3MgI$, $CH_3CH_2MgBr$ and $CH_3CH_2CH_2MgI$ can be used. Grignard reagent is not limited to these compounds as a matter of course.

Reaction conditions between a Grignard reagent and a halogenated borazine compound are not particularly limited. For example, a certain kind of halogenated borazine compound and diethyl ether as a solvent are charged into a reactor under the nitrogen atmosphere. Into the reaction solution, $CH_3MgI$ as a Grignard reagent is slowly added drop-wise while the reaction solution is stirred. An amount slightly exceeding theoretically necessary amount of Grignard reagent is added drop-wise, the reaction solution is then stirred for further 1 hour. The borazine compound represented by the Chemical Formula 2 can be obtained through such steps.

In the resultant borazine compound of Chemical Formula 2, certain levels of halogen and metal can be contained. Halogen can be mixed into a borazine compound by various causes, and main origins include, for example, halogen element contained in the halogenated borazine compound and halogen element contained in the Grignard reagent. For example, when B,B',B"-trichloro-N,N',N"-trimethylborazine is used as a halogenated borazine compound, chlorine atom comes to be mixed in the borazine compound. Also, when methyl magnesium bromide is used as a Grignard reagent, bromine comes to be mixed in the borazine compound. Metal can be mixed into a borazine compound by various causes, and main origins include, for example, metal element contained in the Grignard reagent. For example, when methyl magnesium bromide is used as a Grignard reagent, magnesium comes to be mixed in the borazine compound. Technique to reduce contents of halogen elements or metal elements includes washing and/or purification of the borazine compound.

In preparing a film-forming composition, halogen or metal, preferably both thereof are removed. Preferably, washing and purification is used. When a borazine compound represented by the Chemical Formula 2 is prepared using a halogenated borazine compound represented by the Chemical Formula 4 as a raw material, unreacted halogenated borazine compound is remained in the reaction system in addition to a borazine compound of the desired compound. Compounds other than the borazine compound may be removed using a purification method such as sublimation purification and distillation purification. However, since halogenated borazine compound and borazine compound have similar physical properties, an efficient purification is hindered. For example, when a borazine compound is purified using sublimation purification, since a sublimation temperature of a halogenated borazine compound and a sublimation temperature of a borazine compound come very close to each other, separation efficiency could be lowered.

In order to improve the separation efficiency, the borazine compound represented by the Chemical Formula 2 synthesized can be washed with water, then purified. Up to now, a borazine compound of the Chemical Formula 2 has been thought to have low water resistance and decompose by contacting with water (see, for example, Earl L. Muetterties, "BORON HYDRIDE CHEMISRY", Academic Press, p. 257-259). In fact, a halogenated borazine compound represented by the Chemical Formula 4 decomposes by contacting with water. The inventors of the present invention have, however, found that a borazine compound represented by the Chemical Formula 2 hardly decomposes by contacting with water. Halogenated borazine compound as an impurity is decomposed with washing water. Meanwhile, a whole or a large part of the borazine compound of the desired product remains. Physical properties of fragments from a decomposed halogenated borazine compound greatly differ from those of the borazine compound. Therefore, impurities derived from the halogenated borazine compound can be efficiently removed by a purification method such as sublimation purification and distillation purification, and a borazine compound containing significantly reduced amounts of impurities can be obtained.

Procedures when washing and purification are combined are not particularly limited so long as purification is carried out after washing. For example, a borazine compound synthesized is subjected to 3 steps of washing, first sublimation purification and second sublimation purification. In this case, decomposition of the halogenated borazine compound is intended by washing with water. After that, sublimation purification is repeated to obtain a high purity of borazine compound. In some cases, distillation purification may be carried out instead of the sublimation purification. Embodiments of sublimation purification and distillation purification are similar to those in the case of the borazine compound of the Chemical Formula 1.

Other technique to reduce contents of halogen elements or metal elements includes a method where a borazine compound is purified 3 times or more. The present inventors studied on purification of a borazine compound, and have found that impurities which cannot be sufficiently removed by the first and the second purifications can be dramatically removed by the third purification, though mechanism thereof is not clear.

Washing is conducted preferably using water with lower contents of halogen elements and/or metal elements. Preferably washing is conducted with water having a content of 0.5 ppm or less of each halogen element and a content of 1 ppb or less of each metal element, and more preferably washing is conducted with water having a content of 0.05 ppm or less of each halogen element and a content of 0.1 ppb or less of each metal element.

Embodiment of washing is not particularly limited so long as impurities such as halogenated borazine compound can be removed by washing water. For example, the borazine compound is washed using a separating funnel filled with an organic solvent such as toluene dissolving the borazine compound obtained and ion-exchanged water. Amount of washing water to be used may be decided depending on amount of the borazine compound to be washed and embodiment of the washing. Washing may be carried out twice or more, if necessary.

In this connection, the borazine compound represented by the Chemical Formula 3 can be obtained by producing and purifying according to the similar methods to those for the borazine compound represented by the Chemical Formula 1 or the Chemical Formula 2 described above.

After obtaining a composition comprising the borazine compound represented by any one of the Chemical Formulas 1 to 3 having lower contents of halogen elements and/or metal elements as described above, a low dielectric constant film is formed by a chemical vapor deposition (CVD) method.

In the CVD method, a raw material gas of a film-forming composition comprising the borazine compound represented by any one of the Chemical Formulas 1 to 3 is transferred using a carrier gas such as helium, argon and nitrogen. In this case, property of a film to be formed may be controlled as desired by mixing a compound such as methane, ammonia or alkylamines in the carrier gas.

Flow rate of the carrier gas is preferably 100 to 1,000 sccm. Too low flow rate of the carrier gas extremely extends a time to obtain a desired film thickness, and could disturb proceeding of film-formation. In addition, too high flow rate of the carrier gas could impair uniformity of film thickness in a substrate plane.

Flow rate of the raw material gas comprising the borazine compound is preferably 20 to 300 sccm. Too low flow rate of the gas comprising the borazine compound extremely extends a time to obtain a desired film thickness, and could disturb proceeding of film-formation. In addition, too high flow rate of the gas comprising the borazine compound could lower adhesive property because a film with low cross-linking density is formed.

Flow rate of a gas such as methane and amines is preferably 5 to 100 sccm. Too high flow rate of a gas such as methane and amines could increase dielectric constant of the film to be obtained.

Film is formed by deposition of the above raw material gas transferred in the vicinity of a substrate as described above on the substrate accompanying with chemical reaction. In order to facilitate the chemical reaction efficiently, heat, plasma, laser beam or the like can be used, and these may be used in combination. When heat is used, temperature of the raw material gas and temperature of a substrate are preferably controlled at a temperature between room temperature and 400° C. In this connection, too high temperature of a substrate extremely extends a time to obtain a desired film thickness, and could disturb proceeding of film-formation.

Further, when plasma is used, a substrate is placed in a parallel flat plate type of plasma generator, into which the above raw material gas is introduced. Frequency of RF to be used here is 13.56 MHz or 400 kHz, and power may be optionally set in a range of 5 to 500 W. These two types of RFs having different frequencies may be used in combination. In this connection, too large power of RF to be used for performing the plasma CVD increase a probability of decomposition of the borazine compound represented by any one of the Chemical Formulas 1 to 3 by plasma, and makes difficult to obtain a desired film having the borazine structure. Further, when light is used, deep UV rays or the like obtained from KrF excimer laser or a low-pressure mercury lamp is used in an introducing pathway for the raw material gas or on a substrate surface.

A low dielectric constant film can be formed by the CVD, and dielectric constant of the low dielectric constant film to be formed is preferably 3.0 or less, and more preferably 2.5 or less. Dielectric constant in this range can greatly reduce signal delay. Dielectric constant of the low dielectric constant film can be measured using an impedance analyzer, a LCR meter or the like, after film-formation on a metal film or on a low resistance silicon substrate. In this connection, when measured value varies depending on an equipment to be used or measuring conditions, a value measured by the method described in Examples is employed as a dielectric constant.

EXAMPLES

Example 1

Dehydrated methylamine hydrochloride (33.5 g) and triglyme (98.6 g) as a solvent were charged into a reactor equipped with a condenser under a nitrogen purge, and the mixture was heated to 100° C. A liquid mixture of sodium boron hydride (21.0 g) and triglyme (88.7 g) was added over 1 hour while temperature was maintained at 100° C., the reaction solution was then heated to 180° C. over 2 hours, followed by maturation at 180° C. for further 2 hours.

Subsequently, temperature of the reaction solution was raised from 180° C. to 210° C. to take out N,N',N''-trimethylborazine formed by distillation, and the resultant N,N',N''-trimethylborazine was distilled again to obtain purified N,N',N''-trimethylborazine as a composition for chemical vapor deposition film-formation of Example 1.

Comparative Example 1

The same procedures were repeated as in Example 1 described above except that the distillation purification was carried out only one time, to obtain N,N',N''-trimethylborazine as a composition for chemical vapor deposition film-formation of Comparative Example 1.

[Measurement of Contents of Impurities]

Contents of halogen elements and metal elements in N,N',N''-trimethylborazine obtained in the above Example 1 and Comparative Example 1 were measured. Values obtained by the measurements are shown in the following Table 1. In this connection, in the above Example 1 and Comparative Example 1, an ion chromatography equipment, ICS-1500 (produced from Nippon Dionex K.K.) was used for the measurement of content of halogen element. Also, ELAN DRCII (produced from PerkinElmer Japan Co. Ltd.) which is an ICP-MS (high-frequency emission mass spectrometer) was used for the measurement of content of metal element.

[Film-formation Using Composition for Chemical Vapor Deposition Film-formation and Measurement of Dielectric Constants of the Films Obtained]

Firstly, a silicon wafer evaporated with gold (lower electrode) was prepared. Then, each of N,N',N''-trimethylborazine obtained in the above Example 1 and Comparative Example 1 was introduced into a reactor, in which the above lower electrode was placed, through a heated introducing tube using argon as a carrier gas. In this case, the reaction gas in the reactor was converted to plasma with RF of frequency 13.56 MHz operated at 100 W. In addition, the substrate was heated to 300° C., and vapor temperature of the raw material gas comprising N,N',N''-trimethylborazine was set at 150° C. Further, on the resultant film, a circular pattern of gold electrode having a diameter of 0.3 to 1.5 mm was formed by means of a spattering method as an upper electrode. Capacitance between the upper and the lower electrodes was measured at 1 MHz, and the resultant capacitance was divided by upper electrode area and integrated for film thickness, to calculate dielectric constant. As a result, dielectric constant of the film formed using the composition of Example 1 was 2.50, whereas dielectric constant of the film formed using the composition of Comparative Example 1 was 3.08.

TABLE 1

|  | Content of halogen element (ppb) | | Content of metal element (ppb) | | | | Dielectric constant |
|---|---|---|---|---|---|---|---|
|  | Cl | Br | Na | Al | K | Ca |  |
| Example 1 | 47 | 12 | 35 | 21 | 19 | 26 | 2.50 |
| Comparative Example 1 | 590 | 253 | 289 | 130 | 154 | 192 | 3.08 |

Example 2

Whole amounts of monometylamine hydrochloride (468 g; 6.931 mole) and chlorobenzene (2,000 mL) were charged into a 3 L five-necked round bottom flask. Into this flask, boron trichloride (870 g; 7.389 mole) directly taken out from a gas bomb was added dropwise over 20 hours, while liquefied at −70° C. After completion of the addition, the reaction solution was matured at a temperature of 125 to 135° C. for 60 hours, to complete the synthesis reaction of B,B',B''-trichloro-N,N',N''-trimethylborazine (TCTMB) as a halogenated borazine compound.

After the reaction solution was cooled down to 25° C., the reaction solution was filtered, and the precipitation remaining on the filter paper was washed. The filtrate was transferred to a round-bottom flask, and the solvent was distilled off using an evaporator, to obtain a solid comprising TCTMB. Yield of the solid was 145 g.

The resultant TCTMB (140 g) and diethyl ether (300 ml) as a solvent were charged into a 2 L five-necked flask under a nitrogen atmosphere. A solution of methyl magnesium bromide as a Grignard reagent in diethyl ether (3 M, 800 ml) was added dropwise over 5 hours, while an internal temperature of the reaction system was controlled within a range of 20 to 35° C. After that, the reaction solution was refluxed for 3 hours for maturation to promote the synthesis reaction of hexamethylborazine. After the reaction solution was cooled down to room temperature, the reaction solution was filtered and concentrated to obtain solid A.

The resultant solid A was once subjected to a sublimation purification, to obtain solid B. The thus obtained solid B (7.59 g) was dissolved in toluene, and the resultant toluene solution transferred to a separation funnel was washed with ion-exchanged water (30 ml) 3 times. The toluene layer was taken out from the separation funnel and concentrated, to obtain solid C (7.58 g). The resultant solid C was subjected to sublimation purification twice, to obtain a composition for chemical vapor deposition film-formation comprising hexamethylborazine (HMB). Sublimation conditions were 90° C. and 0.5 kPa.

On the resultant composition, contents of impurities were measured. Contents of chlorine atom and bromine atom were 5 ppm and 1 ppm, respectively. In addition, content of magnesium was 50 ppb or less (Table 2). In this connection, in the measurement of contents of impurities in the compositions, ion chromatography equipment for measurement of amounts of halogen elements and a high-frequency plasma emission spectrometer (ICP) for measurement of contents of metal elements were used, respectively.

Measuring equipment and measuring conditions in Example 2, and the following Example 3, Comparative Example 2 and Comparative Example 3 were as follows:
[Ion Chromatography]

Amount of halogen element was measured using DX-500 produced from Nippon Dionex K.K. As for the columns, IonPac AS4A-SC as a separation column and IonPac AG4A-SC as a guard column were used, respectively. As for eluting solution, 1.8 mmol/liter of $Na_2CO_3$ solution and 1.7 mmol/liter of $NaHCO_3$ solution were used, respectively. Flow rate of the eluting solution was 1.5 ml/min. Amount of sample to be injected was 25 μliter.
[Metal Element Analysis]

Contents of metal elements were measured using ICP or atomic absorption. As for ICP, SPS 4000 produced from Seiko Instruments Inc. was used. As for atomic absorption, 4110 ZL (produced from PerkinElmer Japan Co., Ltd.) was used. Magnesium was measured using ICP because magnesium is detected sensitively by ICP, and other elements were measured using atomic absorption. Measurement by ICP was carried out using a sample diluted ten fold with DMSO/MeOH. Setting of the equipment were as follows; Measuring wavelength: 279.553 nm, RF output: 1.80 kW, and flow rate of carrier gas (Ar): 0.6 L/min. Measurement of atomic absorption was carried out using a sample diluted ten fold with ultrapure water. Wavelength and furnace program for each element were as shown below.

| Measurement Wavelength (nm) | Lamp Current (mA) | Furnace program (° C.) | | | | |
|---|---|---|---|---|---|---|
| | | Drying Temp. 1 | Drying Temp. 2 | Ashing Temp. | Atomization Temp. | Clean Out |
| Ni 232.0 | 25 | 110 | 130 | 1,100 | 2,300 | 2,450 |
| Fe 248.3 | 30 | 110 | 130 | 1,400 | 2,100 | 2,450 |
| Cu 324.8 | 25 | 110 | 130 | 1,100 | 1,900 | 2,450 |
| Cr 357.9 | 25 | 110 | 130 | 1,200 | 2,300 | 2,400 |
| Al 309.3 | 20 | 110 | 130 | 1,200 | 2,300 | 2,450 |
| K 766.5 | 12 | 110 | 130 | 900 | 1,600 | 2,400 |

Just for reference, temperature rising program for nickel is shown below.

| Step | Temperature (° C.) | Ramp Time | Hold Time | Internal Flow |
|---|---|---|---|---|
| 1. Drying 1 | 110 | 1 | 20 | 250 |
| 2. Drying 2 | 130 | 5 | 30 | 250 |
| 3. Ashing | 1,100 | 10 | 20 | 250 |
| 4. Atomization | 2,300 | 0 | 5 | 0 |
| 5. Clean out | 2,450 | 1 | 3 | 250 |

Temperature rising program was appropriately modified depending on the element to be measured, for example, by modifying temperature setting or changing hold time being 3 for Fe and 4 for K.

In addition, the composition obtained in Example 2 was formed to a film in the same manner as in Example 1, and dielectric constant of the resultant film was measured. Dielectric constant of the resultant film was 2.20.

Example 3

The same procedures were repeated as in Example 2 except that a solution of ethyl magnesium bromide in diethyl ether (3.0 M, 800 ml) was used as a Grignard reagent and distillation purification was carried out instead of sublimation purification, to synthesize B,B',B''-triethyl-N,N',N''-trimethylborazine (TETMB).

As for contents of halogen elements and metal elements in B,B',B''-triethyl-N,N',N''-trimethylborazine, chlorine atom was 5 ppm, bromine atom was 1 ppm, Ca, Mn and Mg by ICP measurement were each 50 ppb or less, and Cr, Cu, Fe, Na, Ni and K by atomic absorption measurement were each 50 ppb or less.

Film-formation was performed in the same manner as in Example 1, and dielectric constant of the resultant film was 2.19 (Table 2).

Comparative Example 2

The same procedures were repeated as in Example 2 except that purification was carried out only once, to obtain a composition for chemical vapor deposition film-formation comprising HMB, which contained 115 ppm of chlorine atom and 15 ppm of bromine atom. Film-formation was performed using this composition, and dielectric constant of the resultant film was 3.11 (Table 2).

Comparative Example 3

The same procedures were repeated as in Example 3 except that purification was carried out only once, to obtain a composition for chemical vapor deposition film-formation comprising TETMB, which contained 12,200 ppm of chlorine atom and 15 ppm of bromine atom. Film-formation was performed using this composition, and dielectric constant of the resultant film was 3.08 (Table 2).

TABLE 2

| | Content of Halogen element (ppm) | | Content of Metal element | Dielectric |
|---|---|---|---|---|
| | Cl | Br | (ppb) | Constant |
| Example 2 | 5 | 1 | ≤50 | 2.20 |
| Example 3 | 5 | 1 | ≤50 | 2.19 |
| Comparative Example 2 | 115 | 15 | 600 | 3.11 |
| Comparative Example 3 | 48 | 24 | 12,200 | 3.08 |

The present application is based on JP Application No. 2005-333077 filed on 17 Nov., 2005 and JP Application No. 2005-334494 filed on 18 Nov., 2005, and the disclosures have been incorporated herein by reference in its entirety.

The invention claimed is:

1. A composition for chemical vapor deposition film-formation consisting essentially of a borazine compound represented by the Chemical Formula 1, and a content of each metal element in the composition is 100 ppb or less;

[Chemical Formula 1]

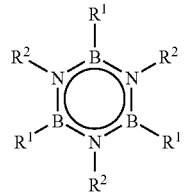

wherein $R^1$ represents a hydrogen atom; $R^2$ represents a methyl group; and wherein a content of chlorine in the composition is 47 ppb or less, and a content of bromine in the composition is 12 ppb or less.

2. A method for production of a low dielectric constant film, comprising forming the composition according to claim 1 into a film using a chemical vapor deposition method.

3. The method according to claim 2, wherein a dielectric constant of the low dielectric constant film is 3.0 or less.

4. The method according to claim 3, wherein the dielectric constant of the low dielectric constant film is 2.5 or less.

* * * * *